(12) United States Patent
Nho et al.

(10) Patent No.: US 8,524,287 B2
(45) Date of Patent: Sep. 3, 2013

(54) **COMPOSITION FOR THE PREVENTION AND TREATMENT OF POSTMENOPAUSAL SYNDROME CONTAINING EXTRACTS OR FRACTIONS OF *ACERIPHYLLUM ROSSII* AS AN EFFECTIVE INGREDIENT**

(75) Inventors: Chu Won Nho, Gangneung-si (KR); Na Ra Jeon, Gangnueng-si (KR); Kyung Su Kang, Gangneung-si (KR); Saet Byoul Lee, Gangneung-si (KR); Ji Hye Yoo, Gwangmyeong-si (KR); Suk Woo Kang, Gangneung-si (KR); Byung Hun Um, Gangneung-si (KR); Cheol-Ho Pan, Gangneung-si (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 12/829,962

(22) Filed: Jul. 2, 2010

(65) Prior Publication Data

US 2011/0206784 A1 Aug. 25, 2011

(30) Foreign Application Priority Data

Feb. 25, 2010 (KR) ........................ 10-2010-0017312

(51) Int. Cl.
*A61K 36/00* (2006.01)
(52) U.S. Cl.
USPC ........................................................ 424/725
(58) Field of Classification Search
None
See application file for complete search history.

(56) References Cited

PUBLICATIONS

"Solutions and Collifative Properties: Mixtures and Solutions". Internet Archive Date: Sep. 22, 2006 [Retrieved from the Internet on: Dec. 18, 2011]. Retrieved from the Internet: <URL:http://web.archive.org/web/20060922000948/http://library.thinkquest.org/C006669/data/Chem/colligative/mixsol.html>.*
Aherne et al. "Lack of Effect of the Flavonoids, Myricetin, Quercetin and Rutin, on Repair of H2O2-Induced DNA Single-Strand Breaks on Caco-2, Hep G2, and V79 Cells". Nutrition and Cancer, vol. 38, No. 1 (2000) 106-115.*
Han et al. "Flavonol Glycosides from the Ariel Parts of *Aceriphyllum rossii* and Their Antioxidants Activities". Arch Pharn Res, vol. 27, No. 4 (2004) 390-395.*
Lysy et al. Hepatology. Nov. 2007;46(5):1574-85.*
Ahn et al. J. Korean Soc. Appl. Biol. Chem. 51(4), 309-315 (2008).*
Han, et al., "Relationship between Fatty Liver and Osteoporosis in Postmenopausal Women", J. Korean Acad. Fam. Med., 2008, 29:114-120.
Oh, "Diabetes and Osteoporosis", Korean Diabetes J., 2009, 33:169-177.
Lobo, "Metabolic Syndrome after Menopause and the Role of Hormones", Maturitas, 2008, 60:10-18.
Akiyama, et al., "Genistein, a Specific Inhibitor of Tyrosine-specific Protein kinases*", The Journal of Biological Chemistry, 1987, 262(12): 5592-5595.
Markovits, et al., "Inhibitory Effects of the Tyrosine Kinase Inhibitor Genistein on Mammalian DNA Topoisomerase II1", Cancer Research, 1989, 49:5111-5117.
Kang, et al., Cancer Suppressing Activity of *Aceriphyllum rossii* Extract Exerted through Induction of G0/G1 Arrest and Apoptosis in HCT116 Human Colorectal Cancer Cells, Cancer Prevention Research, 2009, 14(1):34-39.
Han, et al., "Flavonol Glycosides from the Aerial Parts of *Aceriphyllum rossii* and Their Antioxidant Activities", Arch. Pharm. Res., 2004, 27(4):390-395.
Zheng, et al., "Olean-27-carboxylic Acid-Type Triterpenes with Potent Antibacterial Activity from *Aceriphyllum rossii*", J. Agric. Food Chem., 2008, 56:11752-11756.

* cited by examiner

*Primary Examiner* — Amy L Clark
(74) *Attorney, Agent, or Firm* — Lucas & Mercanti, LLP

(57) ABSTRACT

The present invention relates to a method for the prevention and treatment of postmenopausal syndrome containing the step of administering a pharmaceutically effective dose of the *Aceriphyllum rossii* or its fractions to a subject. The present inventors confirmed that the *Aceriphyllum rossii* extract or its fractions of the invention prepared by using water, alcohol or a mixed solvent thereof could promote the expression of the promoter containing estrogen responsive element (ERE) and accelerated the growth of MCF-7, the human breast tissue originated cell line, suggesting that they had estrogen activity. The inventors further confirmed that the extract or its fractions of the invention had the effect of promoting osteocyte differentiation, so that they could be effectively used for the prevention and treatment of postmenopausal syndrome such as hot flush, osteoporosis and phlebothrombosis caused by estrogen deficiency.

2 Claims, 4 Drawing Sheets

COMPOSITION FOR THE PREVENTION AND TREATMENT OF POSTMENOPAUSAL SYNDROME CONTAINING EXTRACTS OR FRACTIONS OF *ACERIPHYLLUM ROSSII* AS AN EFFECTIVE INGREDIENT

CROSS-REFERENCES TO RELATED APPLICATION

This patent application claims the benefit of priority from Korean Patent Application No. 10-2010-0017312, filed on Feb. 25, 2010, the contents of which are incorporated herein by reference.

BACKGROUND OF THE INVENTION

1. Field of the Invention

The present invention relates to a composition for the prevention and treatment of postmenopausal syndrome containing *Aceriphyllum rossii* extract or its fractions as an active ingredient. More precisely, the present invention relates to a composition or health improving functional food for the prevention and treatment of postmenopausal syndrome comprising *Aceriphyllum rossii* extract or its fractions extracted by using water, alcohol or the mixed solvent of the two as an active ingredient.

2. Description of the Related Art

According to the recent changes in diet and life style of people, metabolic disease increases rapidly not only in Korea but also in every country. As aging progresses, such metabolic disease is accompanied, for example obesity, diabetes, and cardiovascular disease hyperlipidemia and fatty liver. Particularly, females experience rapid decrease of hormone, especially estrogen, after menopause, accompanied by many different side effects, which is called postmenopausal syndrome. Symptoms of postmenopausal syndrome are hot flush, acute changes of heart rate, sleep disorder, neurosis, hypersensitiveness, concentration decrease, depression, anxiety, self-confidence deficiency, sexual desire deficiency, osteoporosis, and atherosclerosis. As an example, osteoporosis is the disease caused by the decrease of bone density and ossein with reducing bone strength, which results frequent fracture even by a light impact. This disease is frequent among females having been through menopause. Those postmenopausal women who have severe fatty liver are more apt to develop osteoporosis and show lower bone density. It has been actually suggested that obesity is closely related to symptoms of postmenopausal syndrome. That is, in postmenopausal women, obesity is closely connected to metabolic disease. The estrogen signal transduction pathway closely relates to not only hormone-dependent disease such as osteoporosis but also metabolic disease (Han et al., 2008, J. Korean Acad. Fam. Med., 29:114-120; Oh, 2009, Korean Diabetes J. 33:169-177; Lobo, 2008, Maturitas, 60: 10-18). To treat postmenopausal syndrome, hormone replacement therapy (HRT) that administrates estrogen artificially into women in menopause has been widely performed.

Estrogen is divided into two groups, which are natural estrogen and synthetic estrogen. The most common method for the administration of the synthetic estrogen is oral administration. However, parenteral administration using transdermal patch, transdermal cream, gel or vaginal cream is also available. But this artificial injection of the synthetic estrogen is controversial because of high risk of uterine cancer, breast cancer, phlebothrombosis, and gallbladder disease according to the long term administration, even though it is effective in improvement of climacteric symptom. Therefore, studies have been actively going on to find out natural estrogen, as an alternative to the synthetic hormone, particularly derived from a plant that carries less side effects but has similar activity to the synthetic estrogen. In particular, the plant originated natural estrogen is called phytoestrogen.

Phytoestrogen indicates a nonsteroidal compound originated from a plant having a similar structure and functions to the female hormone estrogen, which is largely found in stems, roots, flowers and seeds of plants. Phytoestrogen includes isoflavone of bean and kudzu, coumestan of clover, and lignan of flax seed. In addition, flavanones, flavones, and dihydrocalchones are also included in phytoestrogen. Isoflavone exists as inactive glucoside of biochanin A and formononetin in plants. Once it is absorbed in the body, isoflavone is converted into Genistein and daidzein, each having estrogen-like structure, with demonstrating estrogen-like activity. The most representative example of phytoestrogen is Genistein that inhibits protein tyrosine kinase in cells, suggesting that it has anticancer effect resulting in the inhibition of tumor growth (*The Journal of Biological Chemistry.*, 262(12), 5592-5, 1987; *Cancer Research.*, 49, 5111-7, 1989). In the meantime, it has been also reported that Genistein is not effective or even causes cancer in those retain inherited tendency for uterine cancer and breast cancer. Therefore, it is requested to develop a novel phytoestrogen that can complement side effects of Genistein.

*Aceriphyllum rossii* is a perennial herbaceous plant which belongs to Saxifragaceae originated from frigid and temperate zones of Northern Hemisphere. In Korea, it grows in cracks on the rock or cliff near water stream of valley. This plant grows and reproduces by stretching its root stocks in between cracks on the rock. The shape of its leaf is similar to the shape of the maple leaf. The plant bears its flowers in clusters beautifully, which are white with reddish purple, so that it is attracted as an ornamental plant. Particularly, young leaves or soft stems before blooming have been eaten as salad or as cooked, suggesting that the plant is superior to other estrogen alternative plants in safety with less side effects. *Aceriphyllum rossii* has a wide spectrum of pharmaceutical activity and its anti-oxidant activity, anticancer activity and antiviral activity have already been reported (Kang et al., 2009, Cancer Prevention Research, 14(1) 34-39; Han et al., 2004, Arch. Pharm. Res., 27(4) 390-395; Zheng et al., 2008, J. Agric. Food Chem., 56: 11752-11756). However, other activities of *Aceriphyllum rossii* in relation to anti-obesity activity, phytoestrogen activity and osteogenesis promoting activity have not been disclosed, yet.

The present inventors screened another phytoestrogen alternative among domestic native plants, particularly among wild greens, during which a composition comprising *Aceriphyllum rossii* extract or its fractions having activity to estrogen response element (ERE) was identified. And further, the inventors confirmed that the composition had the effect of inducing differentiation into osteoblasts and the effect of inhibiting differentiation into adipocytes. Accordingly, the inventors confirmed that the said composition can not only be used as a hormone alternative composition having phytoestrogen like activity but also be effective in treating metabolic disease such as obesity. At last, the present inventors completed this invention by confirming that the *Aceriphyllum rossii* extract or its fractions have estrogen activity, so that they could be used as a hormone alternative composition for relieving symptoms of postmenopausal syndrome, suggesting that they could be used as a composition for the prevention and treatment of postmenopausal syndrome.

SUMMARY OF THE INVENTION

It is an object of the present invention to provide a method for the prevention or treatment of postmenopausal syndrome containing the step of administering a pharmaceutically effective dose of *Aceriphyllum rossii* extract or its fractions to a subject.

It is another object of the present invention to provide a composition for the prevention and treatment of postmenopausal syndrome or health improving functional food for the improvement of postmenopausal syndrome comprising *Aceriphyllum rossii* extract or its fractions as an active ingredient that can be replaced with synthetic estrogen as an effective hormone alternative method for the prevention and treatment of postmenopausal syndrome.

To achieve the above objects, the present invention provides a method for the prevention or treatment of postmenopausal syndrome comprising the step of administering a pharmaceutically effective dose of *Aceriphyllum rossii* extract or its fractions to a subject.

The present invention also provides a composition for the prevention and treatment of postmenopausal syndrome containing *Aceriphyllum rossii* extract or its fractions as an active ingredient.

In addition, the present invention provides a health improving functional food for the prevention and treatment of postmenopausal syndrome containing *Aceriphyllum rossii* extract of its fractions as an active ingredient.

Advantageous Effect

The *Aceriphyllum rossii* extract or its fractions are wild green originated edible plant having estrogen like activity and the effect of accelerating the differentiation of osteoblasts, so that they can be effectively used as an active ingredient for the composition for hormone replacement therapy (HRP) for the prevention, relief or treatment of postmenopausal syndrome such as hot flush, osteoporosis, and phlebothrombosis caused by the deficiency of estrogen in menopause or for the health improving functional food for the improvement of postmenopausal syndrome.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
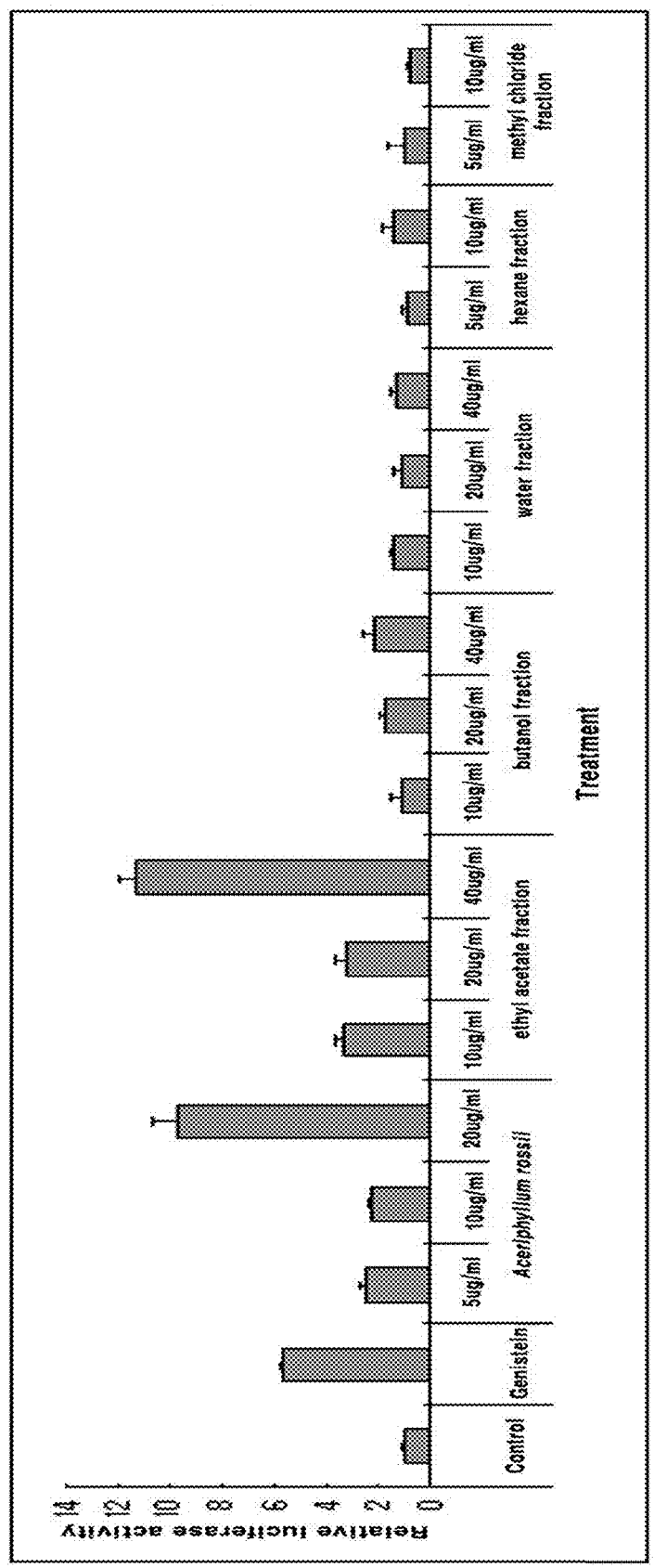
FIG. 1 is a graph illustrating effects of *Aceriphyllum rossii* extract or its fractions on transactivation of estrogen responsive element (ERE). Luciferase activities of MCF-7 cells transfected with ERE-lucifrase construct were measured after treatment of *Aceriphyllum rossii* extract or its fractions.

Hereinafter, the present invention is described in detail.

The present invention provides a method for the prevention or treatment of postmenopausal syndrome containing the step of administering a pharmaceutically effective dose of *Aceriphyllum rossii* extract of its fractions to a subject.

The present invention also provides a method for the prevention or treatment of postmenopausal syndrome containing the step of administering a pharmaceutically effective dose of *Aceriphyllum rossii* extract of its fractions to a subject with postmenopausal syndrome.

The present invention further provides a composition for the prevention and treatment of postmenopausal syndrome containing *Aceriphyllum rossii* extract or its fractions as an active ingredient.

The symptoms of postmenopausal syndrome herein are preferably exemplified by one of hot flush, osteoporosis, and phlebothrombosis, but not always limited thereto.

The *Aceriphyllum rossii* extract of the present invention is preferably prepared by the following steps, but not always limited thereto;

1) extracting dried *Aceriphyllum rossii* with an extraction solvent;
2) filtering the extract of step 1);
3) preparing extract by concentrating the filtered extract of step 2) under reduced pressure; and
4) preparing fractions from the extract of step 3) by using an organic solvent.

In this method, *Aceriphyllum rossii* can be the one that was cultivated, picked up, or purchased on market. The whole plant of *Aceriphyllum rossii* can be used, or leaves, stems or roots can be separately used, which is more preferred but not always limited thereto. The *Aceriphyllum rossii* can be picked from any stage of its life-cycle, but young plants are preferred.

In the above method, the extraction solvent can be selected among water, alcohol and a mixture thereof, but preferably $C_1$-$C_4$ lower alcohol or its mixed solvent is selected. Methanol or ethanol is more preferred as a solvent, but not always limited thereto. The preferable amount of the solvent is 2-30 times the amount of dried *Aceriphyllum rossii*, and more preferably 20 times the amount, but not always limited thereto. The method for the extraction can be selected from the group consisting of hot water extraction, dipping extraction, reflux extraction and ultrasonic extraction, but ultrasonic extraction is preferably selected. Extraction is preferably performed once to 5 times. The temperature of the extraction is preferably 10-100° C., and room temperature is more preferred, but not always limited thereto.

The duration of the extraction is preferably a day to 7 days, and more preferably 3 days to 7 days, but not always limited thereto.

The method for the preparation of the extract can be selected from the group consisting of those methods using an extraction device such as supercritical extraction, subcritical extraction, high temperature extraction, high pressure extraction, and ultrasonic extraction; and the method using an absorbed resin such as XAD and HP-20. The extraction is preferably performed by reflux with increasing temperature or at room temperature, but not always limited thereto. The extraction is preferably repeated 1-5 times and more preferably 3 times, but not always limited thereto.

In this method, the concentration under reduced pressure of step 3) is preferably performed by using rotary vacuum evaporator, but not always limited thereto. The drying herein is preferably performed by reduced-pressure drying, vacuum drying, boiling drying, spray drying, room temperature drying or freeze drying, but not always limited thereto.

In the above method, the organic solvent of step 4) is preferably normal-hexane, ethyl acetate or normal-butanol, but not always limited thereto. The said fractions are preferably normal-hexane fractions, ethyl acetate fractions, normal-butanol fractions or water fractions prepared by suspending *Aceriphyllum rossii* extract in water, followed by fractionating thereof using normal-hexane, ethyl acetate, normal-butanol and water. They are more preferably ethyl acetate fractions, but not always limited thereto. To obtain those fractions, fractionation of *Aceriphyllum rossii* extract is repeated 1-5 times, and preferably 3 times. It is preferred to concentrate the extract under reduced pressure after fractionation, but not always limited thereto.

In a preferred embodiment of the present invention, the dried *Aceriphyllum rossii* was pulverized into a proper size and placed in an extraction vessel. Ethanol was added thereto, and the mixture was boiled, followed by reflux extraction. After standing for a while, the mixture was filtered by filter paper to give ethanol extract. Next, the *Aceriphyllum rossii* extract was fractionated by using n-hexane, ethyl acetate, n-butanol and water stepwise to obtain n-hexane fraction, ethyl acetate fraction, n-butanol fraction or water fraction.

To investigate whether or not the *Aceriphyllum rossii* extract or its fractions had estrogen activity, luciferase activity of MCF-7 (human breast cancer cell line) transfected with pERE-vitallogenin-Luc plasmid was tested to confirm the activation of estrogen responsive element (ERE). As a result, compared with the control group, the *Aceriphyllum rossii* extract and its ethyl acetate fraction demonstrated significant luciferase activity which was increased dose-dependently. When 20 ug/ml of the *Aceriphyllum rossii* extract and 40 ug/ml of ethyl acetate fraction were treated, strong activation of estrogen responsive element was observed, compared with the positive control Genistein (see FIG. 1).

To investigate the effect of the *Aceriphyllum rossii* extract or its fractions on the growth of MCF-7 cells under hormone deficient culture condition, clongenic assay was performed. As a result, the *Aceriphyllum rossii* extract and its ethyl acetate fraction strongly induced the growth of MCF-7 cells, compared with the positive control Genistein (see FIG. 2).

The growth of the human breast cancer cell line MCF-7 is inhibited under hormone deficient culture condition. To the said condition, when estrogen is added, MCF-7 cells start growing actively. So, if a specific element is treated to the hormone deficient condition, it could be investigated whether the specific element has estrogen like activity by measuring the growth of MCF-7 cells in that condition.

To investigate whether the *Aceriphyllum rossii* extract or its ethyl acetate fraction had the effect of promoting the differentiation of osteocytes, the differentiation of osteocytes was induced using C3H10T1/2, mouse embryonic fibroblast cells. Then, the *Aceriphyllum rossii* extract or its ethyl acetate fraction was treated thereto. Von kosa staining that specifically stains the region with calcium accumulated indicating calcific nodule formation was performed to measure the formation of osteocytes.

Figure 3:
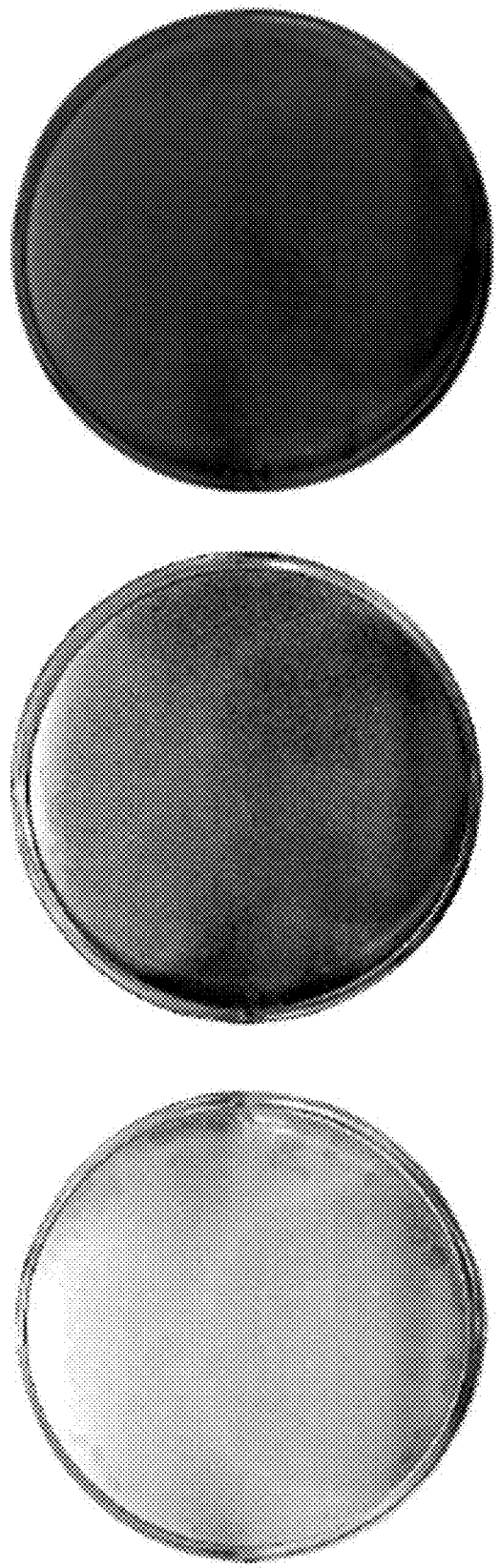
FIG. 3 is a diagram illustrating the stimulatory effects of *Aceriphyllum rossii* extract or its ethyl acetate fraction on the formation of osteocyte, which were confirmed by using Von kosa staining assay.

As a result, compared with the control group, the *Aceriphyllum rossii* extract or its ethyl acetate fraction was confirmed to promote the formation of osteocytes significantly (see FIG. 3).

From the above test results, it was confirmed that the *Aceriphyllum rossii* extract or its ethyl acetate fraction had significant estrogen activity and the effect of promoting osteocyte differentiation. That is, the *Aceriphyllum rossii* extract its fractions of the present invention activate estrogen responsive element and induce the growth of MCF-7, the human breast cancer cell line, and promote osteocyte differentiation.

Therefore, the composition of the present invention containing the *Aceriphyllum rossii* extract or its fractions separately or as a package can be effectively used for the prevention and treatment of the symptoms of postmenopausal syndrome caused by the lack of estrogen, owing to its estrogen activity and its effect of promoting osteocyte differentiation.

The present invention also provides a composition for the prevention and treatment of obesity comprising the *Aceriphyllum rossii* extract or its fractions as an active ingredient.

In a preferred embodiment of the present invention, to investigate whether the *Aceriphyllum rossii* extract or its fractions could inhibit adipocyte differentiation, the differentiation of adipocytes was induced in C3H10T1/2 cells. Then, the *Aceriphyllum rossii* extract or its fractions were treated thereto. Oil Red O staining was performed to dye fat, followed by investigation of the differentiation of adipocytes.

Figure 4:
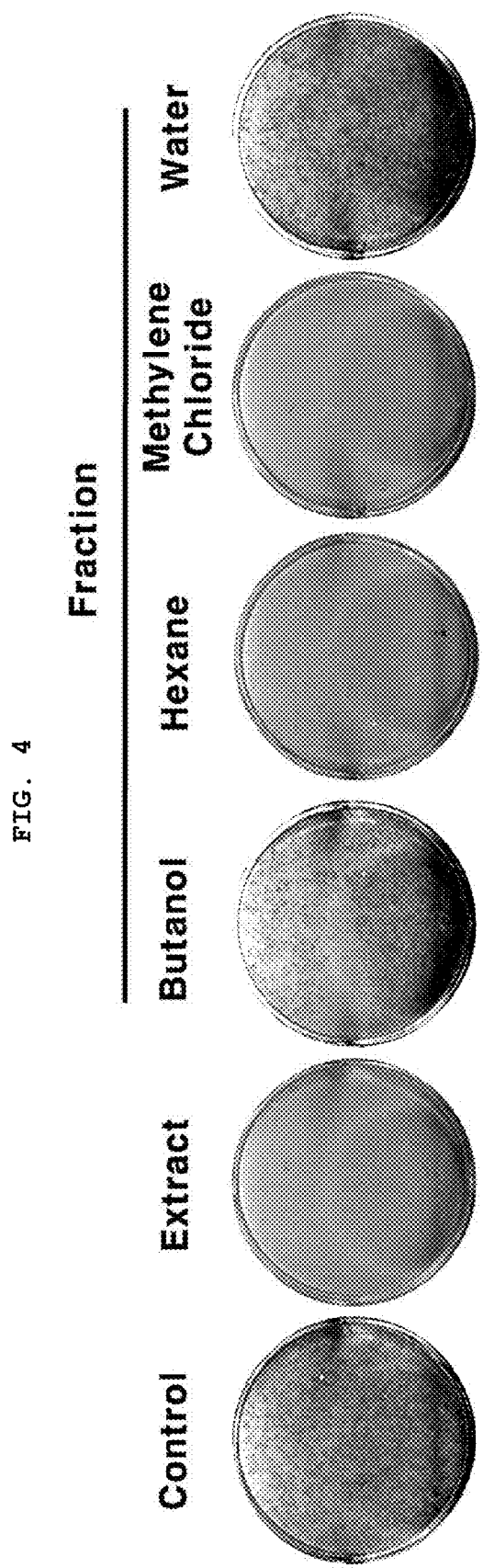
FIG. 4 is a diagram illustrating the inhibitory effects of *Aceriphyllum rossii* extract or its fractions on adipogenesis, which were confirmed by using Oil Red O staining assay.

As a result, compared with the control group, the *Aceriphyllum rossii* extract or its fractions demonstrated significant inhibition effect on the differentiation of adipocytes (see FIG. 4).

Therefore, the *Aceriphyllum rossii* extract or its fractions of the present invention can be effectively used for the prevention and treatment of obesity as well.

The composition comprising the Aceriphyllum rossii extract or its fractions of the present invention preferably contains the *Aceriphyllum rossii* extract or its fractions at the amount of 0.1-50 weight % by the total weight of the composition, but not always limited thereto.

The composition of the present invention can additionally include generally used carriers, excipients and diluents.

The composition of the present invention can be formulated for oral administration, for example powders, granules, tablets, capsules, suspensions, emulsions, syrups and aerosols, and for parenteral administration, for example external use, suppositories and sterile injections, etc. The carriers, excipients and diluents are exemplified by lactose, dextrose, sucrose, sorbitol, mannitol, xylitol, erythritol, maltitol, starch, acacia rubber, alginate, gelatin, calcium phosphate, calcium silcate, cellulose, methyl cellulose, microcrystalline cellulose, polyvinyl pyrrolidone, water, methylhydroxybenzoate, propylhydroxybenzoate, talc, magnesium stearate and mineral oil. Formulations can be prepared by using generally used excipients or diluents such as fillers, extenders, binders, wetting agents, disintegrating agents and surfactant. The solid formulations for oral administration are prepared by mixing one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations, suppositories and injections. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The composition of the present invention can be administered orally or parenterally. Parenteral administration is performed by local administration or systemic administration, systemic administration is more preferred, and intravenous injection is most preferred.

The effective dosage of the composition of the present invention can be determined by those in the art according to weight and condition of a patient, severity of a disease, preparation of a drug, administration pathway and time. The effective dosage of the composition is preferably 0.0001-1 g/kg per day, and more preferably 0.001-200 mg/kg per day. The administration frequency can be once a day or a few times a day. The above dosage cannot limit the scope of the invention in any way.

The present invention further provides a health improving functional food comprising the *Aceriphyllum rossii* extract or its fractions as an active ingredient for the prevention and improvement of postmenopausal syndrome symptoms.

The postmenopausal syndrome symptoms are preferably exemplified by hot flush, osteoporosis and phlebothrombosis, but not always limited thereto.

The *Aceriphyllum rossii* extract or its fractions of the present invention activate estrogen response element, induce the growth of the human breast cancer cell line MCF-7, and promote osteocyte differentiation. Therefore, the *Aceriphyllum rossii* extract or its fractions of the present invention demonstrating the estrogen activity and the effect of promoting osteocyte differentiation can be effectively used for the prevention and improvement of postmenopausal syndrome symptoms caused by estrogen deficiency.

In addition, the present invention provides a health improving functional food comprising the *Aceriphyllum rossii* extract or its fractions as an active ingredient for the prevention and improvement of obesity.

In a preferred embodiment of the present invention, to investigate whether the *Aceriphyllum rossii* extract or its fractions could inhibit adipocyte differentiation, adipocyte differentiation was induced in C3H10T1/2 cells. Then, the *Aceriphyllum rossii* extract or its fractions were treated to the cells, followed by Oil Red 0 staining to dye fat. The differentiation of adipocytes was measured. Compared with the control group, the *Aceriphyllum rossii* extract or its fractions were confirmed to inhibit the differentiation of adipocytes significantly. Therefore, the *Aceriphyllum rossii* extract or its fractions of the present invention can be effectively used for health improving functional food for the prevention and improvement of obesity.

The food herein is not limited. For example, the *Aceriphyllum rossii* extract can be added to drinks, meats, sausages, breads, biscuits, chocolates, candies, snacks, cookies, pizza, ramyuns, noodles, dairy products including ice cream, soups, beverages, alcohol drinks and vitamin complex, etc, and in wide sense, almost every food applicable in the production of health food can be included.

The *Aceriphyllum rossii* extract or its fractions of the present invention can be used as a food additive. In that case, the *Aceriphyllum rossii* extract or its fractions can be added as it is or as mixed with other food components according to the conventional method. The mixing ratio of active ingredients can be regulated according to the purpose of use (prevention or improvement). In general, to produce health food or beverages, the *Aceriphyllum rossii* extract or its fractions are added preferably by 0.1-90 weight part. However, if long term administration is required for health and hygiene or for regulating health condition, the content can be lower than the above but higher content can be accepted as well since the *Aceriphyllum rossii* extract or its fractions have been proved to be very safe.

The composition for health beverages of the present invention can additionally include various flavors or natural carbohydrates, etc, like other beverages in addition to the extract of crude drug complex. The natural carbohydrates above can be one of monosaccharides such as glucose and fructose, disaccharides such as maltose and sucrose, polysaccharides such as dextrin and cyclodextrin, and sugar alcohols such as xylytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1-20 g and more preferably 5-12 g in 100 ml of the composition.

In addition to the ingredients mentioned above, the *Aceriphyllum rossii* extract or its fractions of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The *Aceriphyllum rossii* extract or its fractions of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.1-20 weight part per 100 weight part of the Aceriphyllum rossii extract or its fractions of the present invention.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Preparation of *Aceriphyllum rossii* Extract or its Fractions

The *Aceriphyllum rossii* herein was collected in Pyeongchang and Uljin, Gangwon-do, Korea. The collected *Aceriphyllum rossii* was washed and dried.

The whole plants including leaves, stems, and roots, were pulverized into a proper size, which were placed in an extraction vessel. 70% ethanol was added thereto. After standing for 3-7 days at room temperature, the mixture was filtered by filter paper to obtain *Aceriphyllum rossii* extract. Particularly, 22.5 L of 70% ethanol was added to 4500 g of the dried *Aceriphyllum rossii*, followed by $3^{rd}$ extraction and concentration. As a result, 554 g of extract was obtained. Fractionation of the *Aceriphyllum rossii* extract was performed using n-hexane, methylene chloride, ethyl acetate, n-butanol and water stepwise, resulting in 106.4 g of hexane layer, 39.3 g of methylene chloride layer, 67.7 g of ethyl acetate layer, 160.0 g of n-butanol layer, and 176.3 g of water layer. The *Aceriphyllum rossii* extract or its fractions were dissolved in dimethyl sulfoxide (DMSO) for the further use in the following experiments.

EXPERIMENTAL EXAMPLE 1

Transactivation of Estrogen Response Element by the *Aceriphyllum rossii* Extract or its Fractions of the Present Invention The breast cancer cell line, MCF-7 (American Type of Cell Culture, ATCC), was used to investigate estrogen activity of the *Aceriphyllum rossii* extract or its fractions of the present invention. Particularly, MCF-7 cells were seeded at the density of 1×10⁵ cells/well, followed by culture for 24 hours in a 37, 5% $CO_2$ incubator. The cultured cells were transfected with pERE-vitallogenin-Luc plasmid. After culturing for 24 hours, the cells were treated with the *Aceriphyllum rossii* extract or its fractions dissolved in DMSO, prepared in <Example 1>, at the concentration of 5-40 μg/ml. For the positive control, Genistein (10 μM), phytoestrogen originated from soybean, was used. For the negative control, only DMSO was treated. After treating the extract or its fractions for 24 hours, the cells were lysed and luciferase activity was measured by Dual-Luciferase assay system. The luciferase activity of the experimental group was compared with those of controls. In the Dual-Luciferase assay system, luciferase activity was in proportion to estrogen activity.

As a result, the *Aceriphyllum rossii* extract and ethyl acetate fraction of the present invention increased luciferase activity dose-dependently, compared with the controls. Particularly, when 20 ug/ml of the *Aceriphyllum rossii* extract and 40 ug/ml of ethyl acetate fraction were treated, excellent estrogen activity was confirmed, compared with the positive control Genistein (FIG. 1).

Therefore, it was confirmed that the *Aceriphyllum rossii* extract or its fractions strongly activated estrogen response element, suggesting that they had estrogen activity.

EXPERIMENTAL EXAMPLE 2

Investigation of Cell Growth of MCF-7 after the Treatment of the *Aceriphyllum rossii* Extract or its Fractions of the Present Invention, by Clonogenic Assay The growth of the human breast cancer cell line MCF-7 is inhibited under hormone deficient culture condition. To the said condition, when estrogen is added, MCF-7 cells start growing actively. So, if a specific element is treated to the hormone deficient condition, it could be investigated whether the specific element has estrogen like activity by measuring the growth of MCF-7 cells in that condition.

Cell growth of MCF-7 (American Type of Cell Culture, ATCC) after the treatment of the *Aceriphyllum rossii* extract or its fractions prepared in <Example 1> was investigated by Clonogenic assay. MCF-7 cells were seeded at the density of 1×10³ cells/well, followed by culture for 24 hours in a 37° C., 5% $CO_2$ incubator. The cells were cultured in a medium containing 10% charcoal-dextran treated FBS (CDT-FBS) for 48 hours to avoid being affected by estrogen included in fetal bovine serum (FBS). The estrogen containing medium was replaced every 4 days. For the preparation of the estrogen containing medium, the *Aceriphyllum rossii* extract prepared in <Example 1> was treated at the concentration of 5, 10, and 20 ug/ml, and the fractions thereof were treated at the concentration of 10, 20, and 40 ug/ml. For the positive control, Genistein was treated. For the negative control, DMSO was treated alone. After 12 days from the first treatment, colony formation was observed after staining with Coomasie Brilliant Blue R-250.

Figure 2:
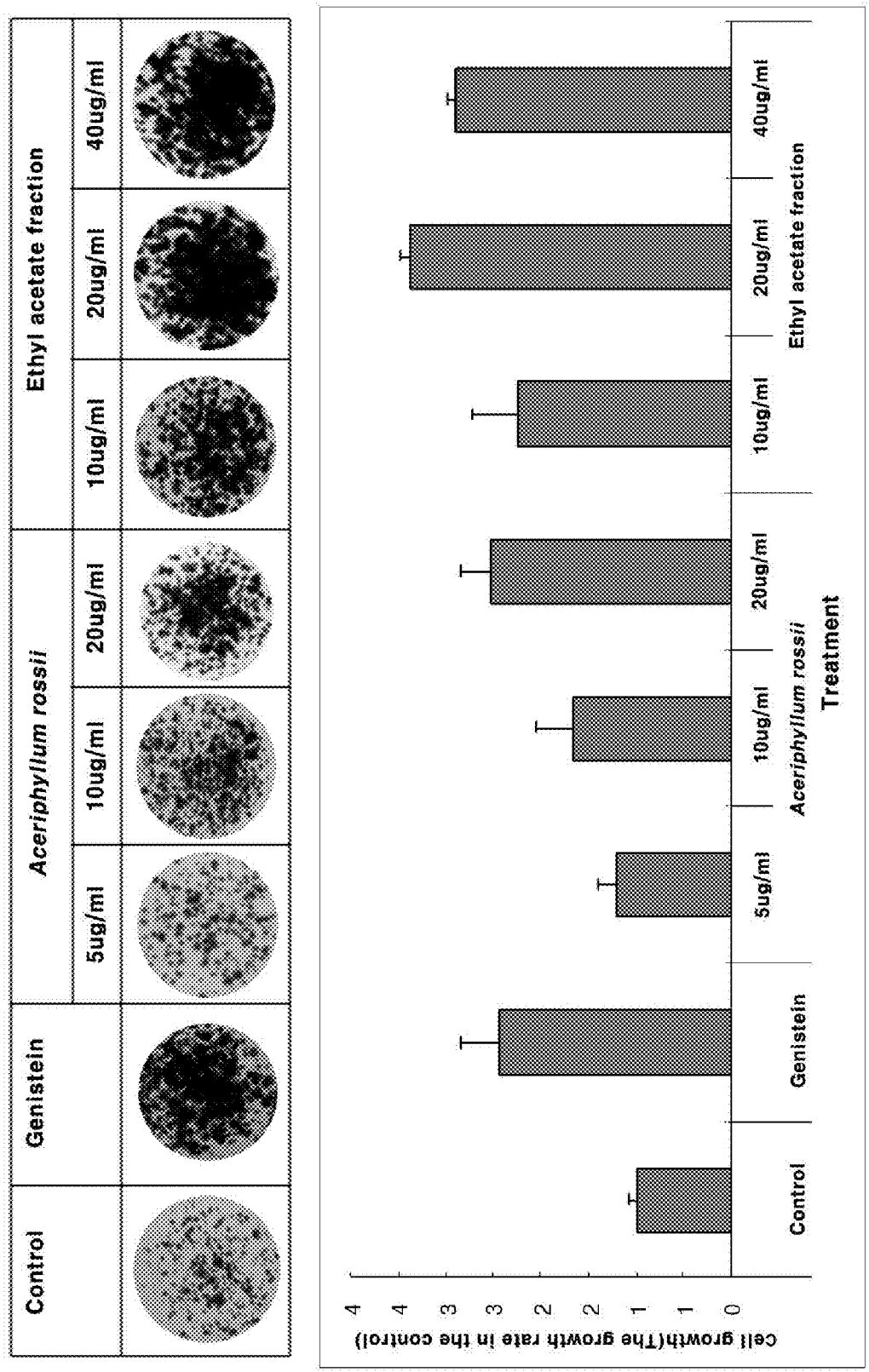
FIG. 2 is set of a diagram and a graph illustrating the proliferation of breast derived MCF-7 cells induced by *Aceriphyllum rossii* extract or its ethyl acetate fraction, which were confirmed by using clonogenic assay.

As a result, it was confirmed that the *Aceriphyllum rossii* extract and ethyl acetate fraction induced the growth of MCF-7 cells significantly, compared with the positive control Genistein (FIG. 2).

Therefore, it was re-confirmed that the *Aceriphyllum rossii* extract or its fractions of the present invention had estrogen activity.

EXPERIMENTAL EXAMPLE 3

Effect of the *Aceriphyllum rossii* Extract or its Fractions of the Present Invention on the Promotion of Osteocyte Differentiation in C3H10T1/2

To investigate whether the *Aceriphyllum rossii* extract or its ethyl acetate fraction had the effect of promoting osteocyte differentiation, the following experiment was performed using mouse embryonic fibroblast C3H10T1/2 (American Type of Cell Culture, ATCC). C3H10T1/2 cells were cultured and maintained in DMEM supplemented with 10% FBS, followed by seeding in 60 mm² culture dish. The culture continued until the cells were fully grown. Then, the medium was replaced with fresh DMEM containing 5% FBS, 3 mM glycerolphosphate, and 50 μg/ml of ascorbic acid, to induce osteocyte differentiation. The medium for differentiation induction was replaced every 2-3 days. The cells were treated with the *Aceriphyllum rossii* extract or its ethyl acetate fraction prepared in <Example 1> at the concentration of 20 μg/ml. For the negative control, DMSO was treated alone. 3-4 weeks after the induction of the differentiation, the cells were fixed with paraformaldehyde. Then, the formation of osteocytes was confirmed by Von kosa staining that specifically stains the region with calcium (Ca2+) accumulated indicating calcific nodule formation.

As a result, it was confirmed that the *Aceriphyllum rossii* extract and its ethyl acetate fraction significantly induced the formation of osteocytes, compared with the control (FIG. 3).

Therefore, it was confirmed again that the *Aceriphyllum rossii* extract or its fractions could promote the differentiation of osteocytes.

EXPERIMENTAL EXAMPLE 4

Inhibitory Effect of Adipocyte Differentiation in C3H10T1/2 by the Treatment of the *Aceriphyllum rossii* Extract or its Fractions of the Present Invention To investigate whether the *Aceriphyllum rossii* extract or its fractions had the inhibitory effect on adipocyte differentiation, the following experiment was performed using C3H10T1/2 cells. C3H10T1/2 cells were cultured and maintained in DMEM supplemented with 10% FBS, followed by seeding in 60 mm² culture dish. The culture continued until the cells were fully grown. Then, the medium was replaced with fresh DMEM containing 10% FBS, 1 pM Dexamethasone, 0.5 mM IBMX (3-isobutyl-1-methylxanthine), and 5 μg/ml of insulin, to induce adipocyte differentiation. 2 days later, the medium was replaced with a fresh one containing 10% FBS and 5 μg/ml of insulin. The medium was replaced every 2 days. The cells were treated with the *Aceriphyllum rossii* extract or its fractions prepared in <Example 1> at the concentration of 20 μg/ml. For the negative control, DMSO was treated alone. 6-8 days after the induction of the differentiation, the differentiation of adipocytes was confirmed by Oil Red O staining.

As a result, it was confirmed that the *Aceriphyllum rossii* extract or its fractions inhibited significantly the differentiation of adipocytes, compared with the control (FIG. 4).

Therefore, it was reconfirmed that the *Aceriphyllum rossii* extract or its fractions of the present invention had the effect of inhibiting the differentiation of adipocytes.

The Manufacturing Examples of the composition comprising the extract of the present invention are described hereinafter, but the present invention is not limited thereto.

MANUFACTURING EXAMPLE 1

Preparation of Powders

| | |
|---|---|
| *Aceriphyllum rossii* extract | 500 mg |
| Lactose | 100 mg |
| Talc | 10 mg |

Powders were prepared by mixing all the above components, which were filled in airtight packs according to the conventional method for preparing powders.

MANUFACTURING EXAMPLE 2

Preparation of Tablets

| | |
|---|---|
| *Aceriphyllum rossii* extract | 500 mg |
| Corn starch | 100 mg |
| Lactose | 100 mg |
| Magnesium stearate | 2 mg |

Tablets were prepared by mixing all the above components by the conventional method for preparing tablets.

MANUFACTURING EXAMPLE 3

Preparation of Capsules

| | |
|---|---|
| *Aceriphyllum rossii* ethyl acetate fraction | 500 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

MANUFACTURING EXAMPLE 4

Preparation of Injectable Solutions

| | |
|---|---|
| *Aceriphyllum rossii* ethyl acetate fraction | 500 mg |
| Sterilized distilled water | proper amount |
| pH regulator | proper amount |

Injectable solutions were prepared by mixing all the above components, putting the mixture into 2 ml ampoules by the conventional method for preparing injectable solutions.

MANUFACTURING EXAMPLE 5

Preparation of Liquid Formulations

| | |
|---|---|
| *Aceriphyllum rossii* ethyl acetate fraction | 100 mg |
| Isomerized sugar | 10 g |
| Mannitol | 5 g |
| Purified water | proper amount |

All the above components were dissolved in purified water. After adding lemon flavor, total volume was adjusted to be 100 ml by adding purified water. Liquid formulations were prepared by putting the mixture into brown bottles and sterilizing thereof by the conventional method for preparing liquid formulations.

MANUFACTURING EXAMPLE 6

Preparation of Health Food

| | |
|---|---|
| *Aceriphyllum rossii* extract | 1000 mg |
| Vitamin complex | proper amount |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food and then the composition for health food was prepared according to the conventional method.

MANUFACTURING EXAMPLE 7

Preparation of Health Beverages

| | |
|---|---|
| *Aceriphyllum rossii* extract | 1000 mg |
| Citric acid | 1000 mg |
| Oligosaccharide | 100 g |

-continued

| | |
|---|---|
| Maesil (*Prunus mume*) Extract | 2 g |
| Taurine | 1 g |
| Purified water | up to 900 ml |

The above constituents were mixed according to the conventional method for preparing health beverages. The mixture was heated at 85 for 1 hour with stirring and then filtered. The filtrate was loaded in 2 liter sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

MANUFACTURING EXAMPLE 8

Preparation of Health Functional Food

<8-1> Preparation of Beverages

| | |
|---|---|
| Honey | 522 mg |
| Thioctic acid amide | 5 mg |
| Nicotinic acid amide | 10 mg |
| Hydrochloric acid riboflavin natrium | 3 mg |
| Hydrochloric acid pyridoxine | 2 mg |
| Inositol | 30 mg |
| Ortho acid | 50 mg |
| *Aceriphyllum rossii* extract | 0.48~1.28 mg |
| Water | 200 ml |

Beverages were prepared based on the above compositions and contents according to the conventional method.
<8-2> Preparation of Chewing Gums

| | |
|---|---|
| Gum base | 20% |
| Sugar | 76.36~76.76% |
| *Aceriphyllum rossii* ethyl acetate fraction | 0.24~0.64% |
| Fruit flavor | 1% |
| Water | 2% |

Chewing gums were prepared based on the above compositions and contents according to the conventional method.
<8-3> Preparation of Candies

| | |
|---|---|
| Sugar | 50~60% |
| Starch syrup | 39.26~49.66% |
| *Aceriphyllum rossii* ethyl acetate fraction | 0.24~0.64% |
| Orange flavor | 0.1% |

Candies were prepared based on the above compositions and contents according to the conventional method.
<8-4> Preparation of Flour Food 0.5~5.0 weight part of *Aceriphyllum rossii* extract was added to the flour. Health enhancing foods such as bread, cake, cookies, crackers and noodles were prepared with the flour mixture according to the conventional method.
<8-5> Preparation of Dairy Products 5~10 weight part of *Aceriphyllum rossii* extract was added to milk. Health enhancing dairy products such as butter and ice cream were prepared with the milk mixture according to the conventional method.
<8-6> Preparation of Sun-Sik Brown rice, barley, glutinous rice and Yulmu (Job's tears) were gelatinized according to the conventional method, dried and pulverized to obtain 60-mesh powders. Black soybean, black sesame and wild sesame were steamed and dried according to the conventional method and pulverized to obtain 60-mesh powders. Sun-Sik was prepared by mixing the dry powders of the grains, seeds and the *Aceriphyllum rossii* ethyl acetate fraction of the present invention according to the below ratio.

| | |
|---|---|
| Brown rice | 30% |
| Yulmu | 15% |
| Barley | 20% |
| Wild sesame | 7% |
| Black soybean | 7% |
| Black sesame | 7% |
| *Aceriphyllum rossii* ethyl acetate fraction | 3% |
| *Ganoderma lucidum* | 0.5% |
| *Rehmannia glutinosa* | 0.5% |

INDUSTRIAL APPLICABILITY

As explained hereinbefore, the *Aceriphyllum rossii* extract or its fractions of the present invention had very clear estrogen activity and the effect of promoting osteocyte differentiation. This extract or its fractions are originated from wild edible greens, so that they not only can be effectively used as an alternative hormone composition for the prevention, alleviation and treatment of postmenopausal syndrome because they are comparatively safer than the synthetic estrogen but also can be effectively used as a composition for the prevention and treatment of obesity owing to their inhibiting effect on adipocyte differentiation.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for promoting differentiation of embryonic fibroblasts and generating osteocytes in vitro comprising treating embryonic fibroblasts with an effective amount of an ethanol extract of *Aceriphyllum rossii* or an ethyl acetate fraction of said ethanol extract.

2. The method of claim 1, wherein the extract is an ethanol extract.

* * * * *